US012571785B2

(12) United States Patent
Brauer et al.

(10) Patent No.: US 12,571,785 B2
(45) Date of Patent: Mar. 10, 2026

(54) SENSOR FOR DETECTING AT LEAST ONE PROPERTY OF A FLUID MEDIUM IN AT LEAST ONE MEASUREMENT CHAMBER

(71) Applicant: Robert Bosch GmbH, Stuttgart (DE)

(72) Inventors: Ingo Brauer, Vaihingen (DE); Karl Wenzel, Stuttgart (DE); Renate Mueller, Reutlingen (DE); Tobias Lang, Stuttgart (DE)

(73) Assignee: ROBERT BOSCH GMBH, Stuttgart (DE)

(*) Notice: Subject to any disclaimer, the term of this patent is extended or adjusted under 35 U.S.C. 154(b) by 108 days.

(21) Appl. No.: 18/248,549

(22) PCT Filed: Nov. 8, 2021

(86) PCT No.: PCT/EP2021/080923
    § 371 (c)(1),
    (2) Date: Apr. 11, 2023

(87) PCT Pub. No.: WO2022/106239
    PCT Pub. Date: May 27, 2022

(65) Prior Publication Data
    US 2023/0393108 A1     Dec. 7, 2023

(30) Foreign Application Priority Data
    Nov. 19, 2020    (DE) ..................... 10 2020 214 581.4

(51) Int. Cl.
    *G01L 9/04*        (2006.01)
    *G01L 9/00*        (2006.01)
    (Continued)

(52) U.S. Cl.
    CPC ........ *G01N 33/0027* (2013.01); *G01L 9/0051* (2013.01); *G01N 27/04* (2013.01)

(58) Field of Classification Search
    CPC .................................................. G01N 33/005
    See application file for complete search history.

(56) References Cited

U.S. PATENT DOCUMENTS

| | | | |
|---|---|---|---|
| 6,079,253 A | 6/2000 | Bonne et al. | |
| 10,048,156 B2 * | 8/2018 | Paulitsch ................ | G01M 3/40 |

(Continued)

FOREIGN PATENT DOCUMENTS

| | | |
|---|---|---|
| DE | 102005058830 A1 | 6/2007 |
| DE | 102005058832 A1 | 6/2007 |

(Continued)

OTHER PUBLICATIONS

International Search Report for PCT/EP2021/080923, Issued Feb. 7, 2022.

*Primary Examiner* — Herbert K Roberts
(74) *Attorney, Agent, or Firm* — NORTON ROSE FULBRIGHT US LLP

(57)                ABSTRACT

A sensor for detecting at least one property of a fluid medium in at least one measuring chamber. The sensor includes a sensor element having at least one heatable diaphragm and an electrical measuring bridge. The diaphragm is connected to the electrical measuring bridge. The sensor is furthermore designed to detect an electrical resistance of the measuring bridge. The sensor is designed to detect a pressure of the fluid medium based on the detected electrical resistance of the electrical measuring bridge.

5 Claims, 2 Drawing Sheets

(51) Int. Cl.
    *G01N 27/04*           (2006.01)
    *G01N 33/00*           (2006.01)

(56)               References Cited

U.S. PATENT DOCUMENTS

| | | |
|---|---|---|
| 2005/0049805 A1 | 3/2005 | Bonne et al. |
| 2010/0242573 A1* | 9/2010 | Matsuhama .......... G01N 25/18 |
| | | 73/25.03 |
| 2015/0097260 A1 | 4/2015 | Tu |

FOREIGN PATENT DOCUMENTS

| | | | |
|---|---|---|---|
| DE | 112018004540 T5 | | 5/2020 |
| JP | H08136490 A | | 5/1996 |
| JP | 2004191164 A | * | 7/2004 |
| JP | 2010164367 A | | 7/2010 |
| JP | 2011017624 A | | 1/2011 |
| JP | 2014190878 A | | 10/2014 |
| JP | 2016011889 A | | 1/2016 |
| JP | 2017036935 A | | 2/2017 |
| WO | 2014006648 A1 | | 1/2014 |

* cited by examiner

SENSOR FOR DETECTING AT LEAST ONE PROPERTY OF A FLUID MEDIUM IN AT LEAST ONE MEASUREMENT CHAMBER

BACKGROUND INFORMATION

A plurality of sensors, sensor elements and methods for detecting at least one property of a fluid medium in a measuring chamber are available in the related art. These may essentially refer to any properties of a gaseous or liquid fluid medium wherein one or more properties may be detected. The present invention is described below without restricting further specific embodiments and applications, in particular with reference to sensors for detecting a gas, in particular the $H_2$ content in a measuring gas.

Sensors of the type described here are used in a plurality of fields, for example in automotive engineering, process engineering, chemistry and mechanical engineering, in particular for determining gas concentrations. In this regard, the determination of hydrogen concentrations, for example in an air-hydrogen mixture, plays an important role in the use of hydrogen fuel cell systems, for example. Safety-relevant applications should also be mentioned here. An air-hydrogen mixture is ignitable, for instance, when the hydrogen content is 4%. Sensors for detecting hydrogen may be used in hydrogen fuel cell vehicles, for example, in order to detect hydrogen which has escaped as a result of damage or a defect, for example, and to trigger warning signals and/or protective measures via a link to appropriate systems. Multiple hydrogen sensors are therefore required for each fuel cell vehicle and these are either installed in the exhaust gas system (exhaust) or operate under atmospheric conditions (ambient).

It is possible to refer to a plurality of measuring principles for such hydrogen sensors. These include, inter alia, the following measuring principles: thermal conduction, catalytic pellistor, electrochemical cell, semiconducting metal oxide, chemi-resistor, field-effect transistor.

A sensor for detecting a component of a gaseous fluid containing multiple components is described in German Patent Application Nos. DE 10 2005 058 830 A1 and DE 10 2005 058 832 A1 in each case. The sensor comprises a housing, which delimits a measuring chamber and in which a measuring chip with a heatable diaphragm is accommodated. The principle of the heated hydrogen sensor is based on the different thermal conductivity of the gas components involved. A resultant asymmetry in the thermal system is converted into a voltage signal.

Despite the advantages of the conventional sensors from the related art for detecting at least one property of a fluid medium, they still have potential for improvement.

In current vehicles, the pressure in the exhaust gas system is not detected. As a result, it is not possible to detect whether the exhaust gas system is blocked (e.g., by objects which are introduced intentionally or unintentionally). An increase in pressure in the exhaust gas system might cause damage to components in front of it. In the sensors described, the diaphragm must be very thin and therefore breaks at ca. 1-2 bar positive pressure.

SUMMARY

According to the present invention, a sensor element for detecting at least one property of a fluid medium in a measuring chamber is provided, which at least substantially avoids the disadvantages of conventional sensor elements for detecting at least one property of a fluid medium in a measuring chamber and which is, in particular, designed to also detect the pressure of the fluid medium in addition to the property of the fluid medium, such as the concentration of $H_2$.

A sensor according to an example embodiment of the present invention for detecting at least one property of a fluid medium in at least one measuring chamber comprises a sensor element having at least one heatable diaphragm and an electrical measuring bridge. The diaphragm is connected to the electrical measuring bridge. The sensor is furthermore designed to detect an electrical resistance of the measuring bridge. The sensor is furthermore designed to detect a pressure of the fluid medium based on the detected electrical resistance of the electrical measuring bridge.

Within the context of the present invention, a sensor element is essentially understood to be any device which may detect the at least one property of the fluid medium and which may, for example, generate at least one measuring signal corresponding to the detected property, for example an electrical measuring signal, such as a voltage or a current. The property may be a physical and/or a chemical property, for example. It may also be possible to detect combinations of properties. In particular, the sensor element may be configured to detect at least one property of a gas, in particular the $H_2$ content in a measuring gas. It may also be possible to detect other properties and/or combinations of properties.

According to an example embodiment of the present invention, the sensor element may be equipped, in particular, for use in a hydrogen fuel cell vehicle. The measuring chamber may essentially be any open or closed chamber in which the fluid medium, in particular the measuring gas, is accommodated and/or through which the fluid medium, in particular the measuring gas, flows.

The detection of the electrical resistance may take place, for example, via so-called self sensing.

Within the context of the present invention, a diaphragm may be understood to be a thin structure, which, like a skin or film, has a large planar extent in relation to its thickness.

Detection may be understood, in particular, as a measurement in which the property of the fluid medium is quantitatively ascertained. For example, the proportion of at least one target gas component, such as $H_2$, of a gas, such as air, in the measuring chamber is quantitatively ascertained. The proportion of the at least one target gas component may relate, for example, to a partial pressure and/or a percentage of the target gas component. The proportion of the target gas component may relate, for example, to multiple proportions of a target gas component. In principle, the target gas component may be any gas of which a proportion may be detected in the gas. The target gas component may preferably be hydrogen. In principle, the gas may be any gas, in particular a gas mixture. The gas may preferably be air, in particular within the context of motor vehicles. The measuring chamber may be, for example, a gas cell of the sensor. In principle, a measuring chamber may be understood to be a chamber in which the fluid medium or gas is located and thus contacts the diaphragm.

The sensor may have a housing. The housing has at least one opening via which the sensor element can be contacted by the fluid medium.

Within the context of the present invention, a housing is essentially understood to be any component or a group of components which fully or partially surround the sensor, and/or close it off externally, and which may give the sensor element mechanical stability. In particular, a housing may surround at least one interior space. For example, the housing may at least partially surround the interior space and at least partially separate it from its environment. The housing may be, in particular, entirely or partially produced from at least one of the following materials: a semiconductor material, a plastic material, a metal.

The housing may be a cap wafer. Within the context of the present invention, a cap wafer is understood to be any wafer which at least partially delimits an interior space. The cap wafer may comprise at least one material selected from the group consisting of: silicon, silicon oxide, silicon nitride and silicon carbide.

According to an example embodiment of the present invention, the sensor may be designed for varying an electrical heating voltage applied to the diaphragm, the sensor being designed to detect the property of the fluid medium when a first heating voltage is applied to the diaphragm, the sensor being designed to detect the pressure of the fluid medium when a second heating voltage is applied to the diaphragm, the second heating voltage being lower or higher than the first heating voltage. Accordingly, the heating voltage is altered to determine two different measured variables.

The first heating voltage may be selected such that a temperature of the diaphragm increases, the second heating voltage being selected such that a temperature of the diaphragm remains substantially constant. To measure the thermal conductivity, the measuring bridge is supplied with a heating voltage which is high enough to heat the diaphragm. To measure the pressure, the diaphragm is supplied with a very low voltage so that the diaphragm does not become heated but, at the same time, the increase in resistance may be measured.

According to an example embodiment of the present invention, the electrical measuring bridge may have electrical resistors, the resistors being arranged on the diaphragm in such a way that an electrical resistance value of the resistors is proportional to the pressure of the fluid medium. The detection of the pressure of the fluid medium on the basis of the detected electrical resistance of the electrical measuring bridge is based on the recognition that the diaphragm deforms, and, in particular, bends, when there is a difference in pressure on its upper side and underside. The resistors on the diaphragm become longer and the resistance value therefore increases. Accordingly, the pressure acting on the diaphragm is proportional to the deformation of the resistors and therefore to the resistance value.

The sensor may be designed to generate an adjustment value for the detected property of the fluid medium based on the detected pressure of the fluid medium. The measuring accuracy of the sensor with regard to the gas concentration to be measured can thus be increased.

According to an example embodiment of the present invention, the sensor may furthermore comprise a temperature sensor element, the temperature sensor element being designed to detect a temperature of the sensor element.

The sensor may be designed to detect the property of the fluid medium based on the temperature of the diaphragm. The thermal conductivity of the fluid medium may thus be reliably detected.

According to an example embodiment of the present invention, the sensor may be designed to output an error signal if the detected pressure exceeds or reaches a predetermined threshold value. For example, this may indicate to the control system of a fuel cell vehicle that the pressure in the exhaust gas system is too high, e.g. due to a blockage. At the same time, the sensor, in the context of a self-diagnosis, may signal that the pressures on the measuring diaphragm are impermissibly high before a failure occurs due to rupture.

According to an example embodiment of the present invention, the sensor may furthermore comprise an electrical heating element for heating the diaphragm. A temperature of the diaphragm can therefore be reliably controlled or regulated.

The sensor may be designed to detect the $H_2$ content in a measuring gas.

The information relating to the $H_2$ concentration to be measured in the supplied measuring gas is generated by a sensor element in the form of a thermal-conductivity sensor element. The thermal conductivity of a gas is, in a first approximation, inversely proportional to the root of the mass of the gas molecules, so that gases with light atoms, such as $H_2$ molecules or He atoms, have a significantly greater heat conductivity than air, which consists substantially of $N_2$ and $O_2$ molecules. The greater the measured thermal conductivity, the higher the proportion of light molecules. The measurement of the thermal conductivity is based on the fact that the diaphragm is cooled by the gas to be measured. The greater the thermal conductivity of the gas to be measured, the stronger the cooling of the diaphragm. By measuring the temperature of the diaphragm, it is therefore possible to infer the thermal conductivity of the gas and, indirectly, its $H_2$ content.

BRIEF DESCRIPTION OF THE DRAWINGS

Further optional details and features of the present invention can be found in the description below of preferred exemplary embodiments, which are illustrated schematically in the figures.

DETAILED DESCRIPTION OF EXAMPLE EMBODIMENTS

Figure 1:
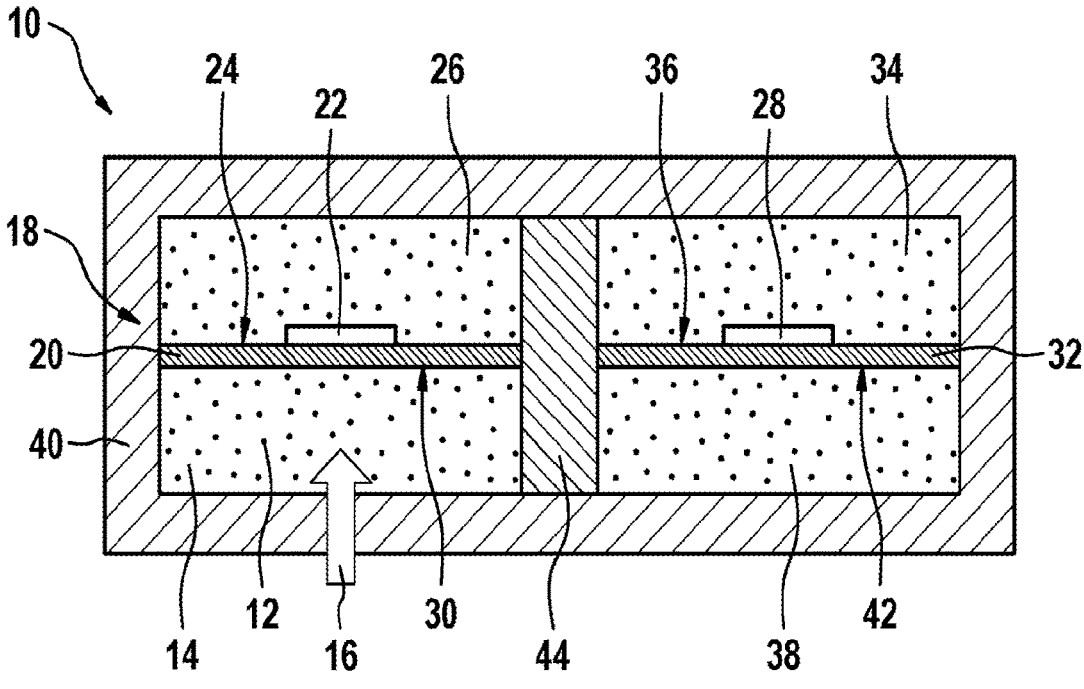
FIG. 1 shows a schematic illustration of a sensor for detecting at least one property of a fluid medium in at least one measuring chamber, according to an example embodiment of the present invention.

FIG. 1 shows a schematic illustration of a sensor 10 for detecting at least one property of a fluid medium 12 in at least one measuring chamber 14, in particular for detecting the $H_2$ content in a measuring gas 16. The sensor 10 may be equipped, in particular, for use in a hydrogen fuel cell vehicle. However, other applications are also possible. The sensor 10 may comprise, in particular, one or more further functional elements (not illustrated in the figures), such as electrodes, electrode supply lines and contacts, multiple layers or other elements. Accordingly, the sensor 10 may be installed in the exhaust gas system of the hydrogen fuel cell vehicle (exhaust) or it may operate under atmospheric conditions (ambient). The measuring chamber may consequently be an exhaust gas system, anode section or interior space of the hydrogen fuel cell vehicle.

The sensor 10 comprises a sensor element 18. The sensor element 18 comprises at least one heatable diaphragm 20. A first electrical heating element 22 is arranged on the diaphragm 20. An upper side 24 of the diaphragm is exposed to a first reference chamber 26, which is closed off from the measuring chamber 14. The first reference chamber 26 is filled with a fluid medium of a known composition. An underside 30 of the diaphragm 20 can be exposed to the fluid medium 12.

The sensor element 18 furthermore comprises a reference diaphragm 32. A further electrical heating element 28 is arranged on the reference diaphragm 32. An upper side 36 of the reference diaphragm 32 is exposed to a second reference chamber 34, which is closed off from the measuring chamber 14. The second reference chamber 34 is filled with a fluid medium of a known composition. An underside 42 of the reference diaphragm 32 is exposed to a third reference chamber 38—this may be the same medium as that in the reference chamber 34—and separated from the fluid medium 12, for example by a media separation apparatus 44. It is explicitly pointed out that the first heating element 22 and the second heating element 28 may be formed in one piece. It is explicitly pointed out that the reference diaphragm 32 is optional. The overall structure may be realized, for example, in the form of a silicon wafer. The sensor 10 may furthermore have a housing 40, in which the sensor element 18 is arranged.

Figure 2:
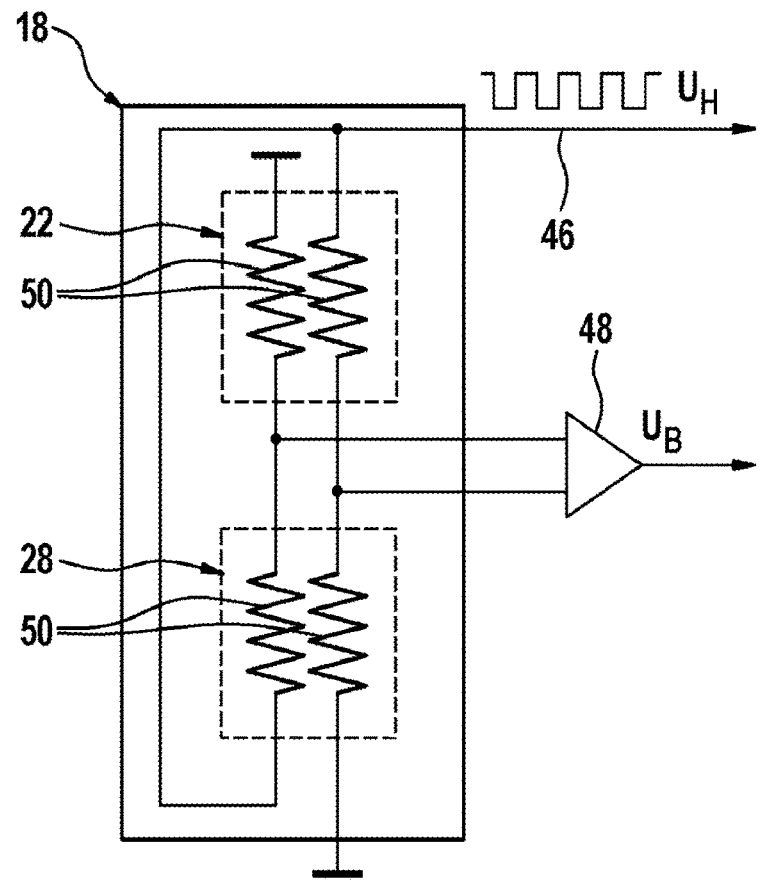
FIG. 2 shows a schematic illustration of an electrical circuit diagram of the sensor element of the sensor, according to an example embodiment of the present invention.

FIG. 2 shows a schematic illustration of an electrical circuit diagram of the sensor element 18 of the sensor 10. This shows the sensor element 18 with the diaphragm 20 and the reference diaphragm 32. An electrical heating voltage $U_H$ can be applied to the first heating element 22 to heat the diaphragm 20 (likewise to the heating element 28 to heat the reference diaphragm 32). The heating voltage $U_H$ is provided by a voltage source 46. The diaphragm 20 and the reference diaphragm 32 are connected to an electrical measuring bridge 48. The measuring bridge 48 is, for example, a Wheatstone bridge. For this purpose, the measuring bridge 49 is formed, for example, by four resistors 50, of which two resistors 50 are arranged on the diaphragm 20 and two resistors 50 are arranged on the reference diaphragm 32. An electrical bridge voltage $U_B$ of the measuring bridge 48 can be tapped at two points between the resistors 50 of the diaphragm 20 and the reference diaphragm 32.

Figure 3:
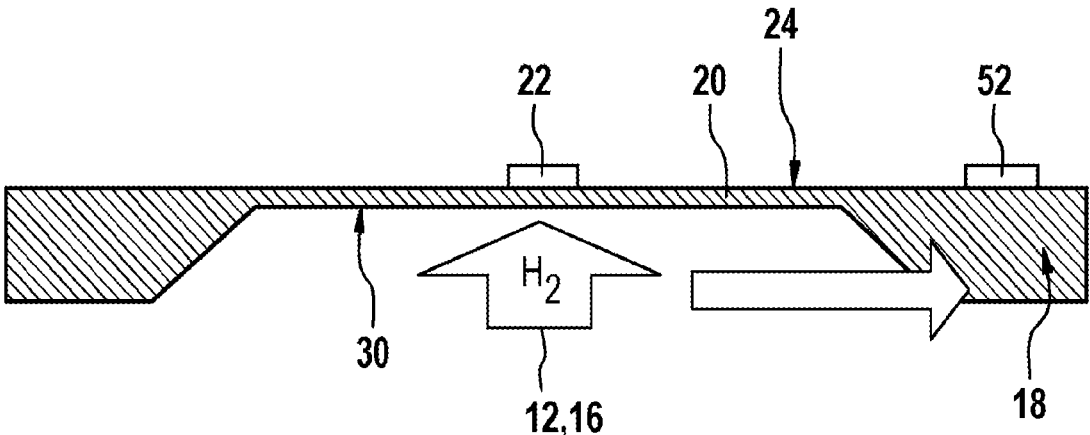
FIG. 3 shows a cross-sectional view of the sensor element, according to an example embodiment of the present invention.

FIG. 3 shows a cross-sectional view of the sensor element 18. The sensor 10 furthermore comprises a temperature sensor element 52. The temperature sensor element 52 is designed to detect a temperature of the sensor element 18 or its silicon chip. To this end, the temperature sensor element 52 is arranged at the edge of the diaphragm 20 or adjacent to the diaphragm 20. The sensor 10 is designed to detect the property of the fluid medium 12 based on the temperature of the diaphragm 20.

Figure 4:
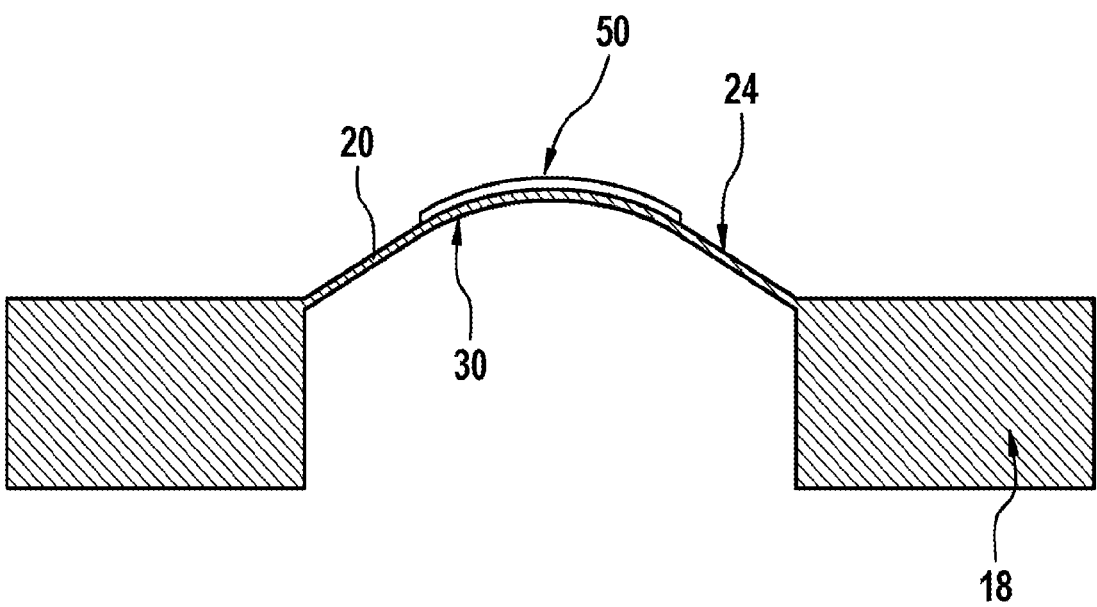
FIG. 4 shows a further cross-sectional view of the sensor element, according to an example embodiment of the present invention.

FIG. 4 shows a further cross-sectional view of the sensor element 18. In particular, FIG. 4 shows the sensor element 18 with a deformed diaphragm 20. The sensor 10 is furthermore designed to detect an electrical resistance of the measuring bridge 48. The sensor 10 is therefore furthermore designed to detect a pressure of the fluid medium 12 based on the detected electrical resistance of the electrical measuring bridge 48. As explained above, the electrical measuring bridge 48 comprises the electrical resistors 50. The resistors 50 are arranged on the diaphragm 20 in such a way that an electrical resistance value of the resistors 50 is proportional to the pressure of the fluid medium 12, as explained in more detail below.

The sensor 10 is designed for varying an electrical heating voltage $U_H$ applied to the diaphragm 20. In particular, the sensor 10 is designed to detect the property of the fluid medium 12 when a first heating voltage $U_H$ is applied to the diaphragm 20. The sensor 10 is designed to detect the pressure of the fluid medium 12 when a second heating voltage $U_H$ is applied to the diaphragm 20, the second heating voltage $U_H$ being lower or higher than the first heating voltage $U_H$. The first heating voltage $U_H$ is selected such that a temperature of the diaphragm 20 increases. The second heating voltage $U_H$ is selected such that a temperature of the diaphragm 20 remains substantially constant or does not increase. The sensor 10 is furthermore designed to generate an adjustment value for the detected property of the fluid medium 12 based on the detected pressure of the fluid medium 12. The sensor 10 is furthermore designed to output an error signal if the detected pressure exceeds or reaches a predetermined threshold value.

A mode of operation or function of the sensor 10 according to the present invention is described below. A first electrical heating voltage $U_H$ is applied to the first heating element 22 to heat the diaphragm 20. In this case, the measuring bridge 48 is supplied with a voltage which is high enough to heat the diaphragm 20. In addition, the reference diaphragm 32 may therefore also be heated by the second heating element 28. With this, different temperatures are established in the region of the diaphragm 20 and the reference diaphragm 32 owing to the different thermal conductivity of the gases which contact the diaphragm 20 and the reference diaphragm 32. The temperature of the sensor element 18 or its silicon chip is detected by the temperature sensor element 52. This temperature corresponds, in a first approximation, to the ambient temperature if the sensor element 18 is not additionally heated. The bridge signal which represents the difference between the temperatures of the measuring diaphragm 20 and the reference diaphragm 32 is tapped as shown in FIG. 2. The measurement of the thermal conductivity is based on the fact that the diaphragm 20 is cooled by the fluid medium 12 to be measured. The higher the thermal conductivity of the fluid medium 12 to be measured, the stronger the cooling of diaphragm 20. By measuring the temperature of the diaphragm 20, it is therefore possible to infer the thermal conductivity of the medium and, indirectly, its $H_2$ level.

To detect the pressure of the fluid medium 12, the sensor 10 alters the heating voltage $U_H$. A second electrical heating voltage $U_H$ is applied to the first heating element 22. In this case, the measuring bridge 48 is supplied with a very low voltage so that the diaphragm 20 does not become heated. If the fluid medium 12 results in a higher pressure on the underside 30 of the diaphragm 20 than on the upper side 24 of the diaphragm 20, the diaphragm 20 bends, as illustrated in FIG. 4. The resistors 50 on the diaphragm 20 become longer and the resistance value therefore increases. The increase in the resistance may be measured when the second heating voltage $U_H$ is applied. The resistance value of the resistors 50 increases with the increase in the pressure difference between the underside 30 and the upper side 24 of the diaphragm 20. For the $H_2$ measurement, the pressure component may be taken into account as an adjustment factor to increase the sensor accuracy.

The present invention may be verified by analyzing the signal of a sensor which is based on a thermal conductivity principle. If such a sensor emits a signal when a pressure is applied, corresponding pressure detection must be available (if a separate pressure sensor is not installed).

The invention claimed is:

1. A sensor configured to detect at least one property of a fluid medium in at least one measuring chamber, the sensor comprising:

a sensor element having at least one heatable diaphragm and a reference diaphragm;

a temperature sensor element, wherein the temperature sensor element is configured to detect a temperature of the sensor element, wherein the sensor is configured to detect the property of the fluid medium based on the temperature of the diaphragm, a first electrical heating element arranged on the at least one heatable diaphragm and configured to heat the diaphragm and a second electrical heating element arranged on the reference diaphragm and configured to heat the reference diaphragm, wherein the at least one heatable diaphragm and the reference diaphragm are connected to an electrical measuring bridge, wherein the electrical measuring bridge includes electrical resistors, wherein the electrical resistors are arranged on the diaphragm in such a way that an electrical resistance of the resistors is proportional to a pressure of the fluid medium, wherein the sensor is configured to detect an electrical resistance of the measuring bridge, wherein the sensor is further configured to detect a pressure of the fluid medium based on the detected electrical resistance of the electrical measuring bridge and wherein the sensor is configured to vary an electrical heating voltage applied to the diaphragm, wherein the sensor is configured to detect the property of the fluid medium when a first heating voltage is applied to the diaphragm, and wherein the sensor is configured to detect the pressure of the fluid medium when a second heating voltage is applied to the diaphragm, wherein the second heating voltage is lower or higher than the first heating voltage.

2. The sensor as recited in claim 1, wherein the first heating voltage is selected such that a temperature of the diaphragm increases, wherein the second heating voltage is selected such that a temperature of the diaphragm remains substantially constant.

3. The sensor as recited in claim 1, wherein the sensor is configured to generate an adjustment value for the detected property of the fluid medium based on the detected pressure of the fluid medium.

4. The sensor as recited in claim 1, wherein the sensor is configured to output an error signal when the detected pressure exceeds or reaches a predetermined threshold value.

5. The sensor as recited in claim 1, wherein the sensor is configured to detect an $H_2$ content in a measuring gas.

* * * * *